United States Patent [19]
Aoki et al.

[11] Patent Number: 5,359,114
[45] Date of Patent: * Oct. 25, 1994

[54] SILANE COMPOUND AND PROCESSES FOR THE PREPARATION THEREOF

[75] Inventors: Tomoko Aoki, Iruma; Satoshi Ueki, Shiki; Tadanao Kohara, Urawa, all of Japan

[73] Assignee: Tonen Corporation, Tokyo, Japan

[ * ] Notice: The portion of the term of this patent subsequent to Aug. 25, 2009 has been disclaimed.

[21] Appl. No.: 41,399

[22] Filed: Mar. 31, 1993

[30] Foreign Application Priority Data

| Apr. 1, 1992 | [JP] | Japan | 4-105260 |
| Apr. 17, 1992 | [JP] | Japan | 4-122783 |
| Apr. 30, 1992 | [JP] | Japan | 4-135636 |
| Apr. 30, 1992 | [JP] | Japan | 4-135637 |

[51] Int. Cl.$^5$ .................. C07F 7/08; C07F 7/18
[52] U.S. Cl. .................... 556/482; 556/469; 556/471
[58] Field of Search .................... 556/482, 469, 471

[56] References Cited

U.S. PATENT DOCUMENTS

5,142,082 8/1992 Sato et al. ................ 556/482
5,175,332 12/1992 Chatterton et al. ........ 556/482

FOREIGN PATENT DOCUMENTS

| 348693 | 6/1989 | European Pat. Off. . |
| 460590 | 12/1991 | European Pat. Off. . |
| 486116 | 5/1992 | European Pat. Off. . |
| 1097988 | 1/1961 | Fed. Rep. of Germany . |

OTHER PUBLICATIONS

Communication/Search Report for European Application No. 93200925.1, Jun. 1993.

*Primary Examiner*—Paul F. Shaver
*Attorney, Agent, or Firm*—Kane, Dalsimer, Sullivan, Kurucz, Levy, Eisele and Richard

[57] ABSTRACT

Novel silane compound, alkoxy cyclopentyl diethoxysilane, is prepared by reacting cyclopentyl trihalosilane with ROH and then with ethanol, or by reacting cyclopentyl triethoxysilane with ROH, wherein alkyl in the alkoxy or R in ROH stands for an organic group selected from tile group consisting of isopropyl, sec-butyl, tert-buryl and tert-amyl groups. The silane compounds are useful as a catalytic component for olefin polymerization and as a silane coupling agent.

8 Claims, 8 Drawing Sheets

SILANE COMPOUND AND PROCESSES FOR THE PREPARATION THEREOF

FIELD OF THE INVENTION

This invention relates to a novel silane compound and processes for the preparation thereof, more specifically a novel silane compound which is suitable as a catalytic component for polymerization of olefin, particularly propylene, or as a silane coupling agent, and processes for the preparation thereof.

PRIOR ART

It is known that a polymer with high stereoregularity can be prepared by the use of alkoxy silanes as a catalytic component in tile polymerization of propylene. However, it was impossible to sufficiently attain both high polymerization activity acid high stereoregularity with known alkoxy silanes as a catalytic component in the polymerization of propylene.

Further, silane compounds are expected to be useful as silane coupling agents and resin modifiers. Accordingly, new silane compounds are awaited.

SUMMARY OF THE INVENTION

One object of the invention is to provide a novel silane compound.

Another object of the invention is to provide processes for the preparation of the novel silane compound.

The present invention provides a silane compound represented by tile following formula (I):

(I)

wherein R represents an organic group selected from the group consisting of isopropyl, sec-butyl, tert-butyl and tert-amyl groups. Thus, the novel silane compound is isopropoxy cyclopentyl diethoxysilane (I-1),
sec-butoxy cyclopentyl diethoxysilane (I-2),
tert-butoxy cyclopentyl diethoxysilane (I-3), and
tert-amyloxy cyclopentyl diethoxysilane (I-4).

The invent ion also provides a process for the preparation of the silane compound represented by the above formula (I), characterized in that cyclopentyl trihalosilane is reacted with ROH, wherein R has the same meaning as above, and then a resultant reaction product is reacted with ethanol.

The invention further provides another process for the preparation of the silane compound represented by the above formula (I), characterized in that cyclopentyl triethoxysilane is reacted with ROH via exchange of alkoxy groups, wherein R has the same meaning as above.

DETAILED DESCRIPTION OF THE INVENTION

These silane compounds (I-1) to (I-4) have tile following boiling points:
(I-1) 115° C./92 mmHg,
(I-2) 130° C./20 mmHg,
(I-3) 90.1° C./8.1 mmHg, and
(I-4) 132° C./24 mmHg.

The structures of these silane compounds may be confirmed by GC-MS, $^1$H-NMR, infrared absorption spectrum (IR) and so on.

When silane compounds (I-1) to (I-4) are analyzed by $^1$H-NMR, signals are observed at δ 0.5 to 2.2 for the cyclopentyl group, and —CH$_3$ of the isopropoxy group and the ethoxy group and δ 3.4 to 4.5 for —CH of the isopropoxy group and —CH$_2$— of the ethoxy group in the case of compound (I-1);

δ 0.5 to 2.2 for the cyclopentyl group and the hydrogen atoms except ones bound to the carbon atoms directly bound to the oxygen atoms in the ethoxy and sec-butoxy groups, and δ 3.5 to 4.1 for the hydrogen atoms bound to the carbon atoms directly bound to the oxygen atoms in the ethoxy and sec-butoxy groups in the case of compound (I-2);

δ 0.5 to 2.0 for the cyclopentyl group, the tert-butoxy group and —CH$_3$ of the ethoxy groups, and δ 3.78 for —CH$_2$ of the ethoxy group in the case of compound (I-3); and δ 0.5 to 2.0 for the cyclopentyl group, tert-amyloxy group and —CH$_3$ of the ethoxy groups, and δ 3.5 to 4.0 for —CH$_2$— of the ethoxy group in the case of compound (I-4) .

In analysis by IR spectra, a large absorption due to the SiOC bonds is observed around 1,100 cm$^{-1}$ in every compound.

Olefinic polymers, such as polypropylene and polybutene, with high stereoregularity can be prepared at high polymerization activity using the silane compound (I) as a catalytic component.

As the silane compound (I) has hydrolyric groups, it can be used as a silane coupling agent, a polymerizable monomer and a resin modifier.

The invention also provides a process for the preparation of the novel silane compound represented by the aforesaid formula (I), wherein cyclopentyl trihalosilane is reacted with ROH, wherein R has the same meaning as defined above, and a resultant reaction product is reacted with ethanol. The starting material, cyclopentyl trihalosilane is represented by the following formula (II):

(II)

wherein X stands for a halogen atom, preferably Cl or Br. It may easily be prepared from cyclopentene and trihalosilane, i.e., H—SiX$_3$ through hydrosilylation reaction:

$$\text{cyclopentene} + \text{H-SiX}_3 \longrightarrow \text{cyclopentyl-SiX}_3 \quad \text{(Reaction A)}$$
$$\text{(II)}$$

In the above reaction, 0.9 to 1.1 moles of trihalosilane may be used per mole of cyclopentene. The reaction is conducted in conditions of a temperature of 100° to 200° C. and 10 minutes to 10 hours, preferably with tile use of a platinum catalyst such as chloroplatinic acid and platinum-1,1,3,3-tetramethyl-1,3-divinyldisiloxane complex. Solvents may also be used, such as benzene and toluene.

In the invention, tile cyclopentyl trihalosilane (II) is reacted with ROH, wherein R has the same meaning as defined above, as follows:

$$\text{cyclopentyl-SiX}_3 + \text{ROH} \longrightarrow \text{cyclopentyl-SiX}_2\text{OR} + \text{HX} \quad \text{(Reaction B)}$$
$$\text{(II)} \hspace{5em} \text{(III)}$$

In the above reaction, 1 to 3 moles of ROH may be used per mole of cyclopentyl trihalosilane (II). The reaction may be carried out at a temperature of, for instance, 20° to 100° C. for 10 minutes to 5 hours, preferably at a temperature of 40° to 70° C. for 30 minutes to 2 hours. Solvents may be used, such as organic solvents, for instance, hexane, ethers, petroleum ether and benzene.

In the invention, it is preferred to use a hydrogen halide acceptor in the reaction mixture in order to facilitate the reaction. Examples of the hydrogen halide acceptor include tertiary amines, and nitrogen-containing heterocyclic compounds such as pyridine, quinoline and isoquinoline with pyridine and quinoline being preferred. 1 to 1.5 Moles of the hydrogen halide acceptor are preferably used per mole of cyclopentyl trihalosilane.

The resultant reaction product (III) is then reacted with ethanol according to the invention to prepare the silane compound (I) of the invention as follows:

$$\text{cyclopentyl-SiX}_2\text{OR} + 2\text{C}_2\text{H}_5\text{OH} \longrightarrow \quad \text{(Reaction C)}$$
$$\text{(III)}$$

$$\text{cyclopentyl-Si(OC}_2\text{H}_5)_2\text{OR} + 2\text{HX}$$
$$\text{(I)}$$

In the above reaction, 2 to 3 moles of ethanol may be used per mole of the compound (III). The reaction may be carried out at a temperature of 0° to 100° C. for 10 minutes to 5 hours, preferably a temperature of 10° to 60° C. for 30 mixtures to 2 hours. It is preferred to use a hydrogen halide acceptor also in Reaction C in order to facilitate the reaction. The hydrogen halide acceptors mentioned for Reaction B may be used also here. A hydrogen halide acceptors used here may be the same as or different from one used in Reaction B, but is generally the same as that. 2 to 3 Moles of a halogen halide acceptor are preferably used per mole of the compound (III).

In the above reactions B and C, an inert gas may be blown in to remove formed hydrogen halide from the reaction system so as to facilitate the reactions.

The novel silane compound (I) may be prepared at high yield in the aforesaid process.

The invention also provide another process for the preparation of the silane compound represented by the formula (I), wherein cyclopentyl triethoxysilane is reacted with ROH via exchange of alkoxy groups, wherein R has the same meaning as defined above.

$$\text{cyclopentyl-Si(OC}_2\text{H}_5)_3 + \text{ROH} \longrightarrow \quad \text{(Reaction D)}$$
$$\text{(IV)}$$

$$\text{cyclopentyl-Si(OC}_2\text{H}_5)_2\text{OR} + \text{C}_2\text{H}_5\text{OH}$$
$$\text{(I)}$$

1 to 20 moles of ROH may be used per mole of the compound (IV). The reaction may be carried out at a temperature of 0° to 100° C. (or 0° to 150° C. for compounds I-2 and I-4), for 10 minutes to 20 hours (or 10 minutes to 50 hours for compound I-3, or 10 minutes to 30 hours for compound I-4). In this alkoxy groups exchange reaction, catalyst may be used such as acids, for instance, trifluoroborane-ether complexes and toluene sulfonic acid, or ones which react with alcohol to form acid, such as trimethyl chlorosilane; or bases, for instance, alkali metal alkoxides and metal hydroxides.

The startling material, cyclopentyl triethoxysilane (IV), may be prepared by reaction of cyclopentyl trichlorosilane with ethanol to form hydrogen halide.

The invention will further be explained with reference to the following Examples, but the invention shall not be limited by the Examples.

EXAMPLES

The $^1$H-NMR and IR measurements were conducted in the following conditions.

$^1$H-NMR
Unit: HITACHI R-24B (Hitachi Seisakusho)
Solvent: CCl$_4$
Standard reference material: CHCl$_3$ and tetramethylsilane (TMS)
IR
Unit: 1600 Series FT-IR (Perkin Elmer)
Method: liquid film method (KBr plate).
GC-MS
HP 5970 B (Hewlett-Packard) was used.

Example 1

Preparation of Isopropoxy Cyclopentyl Diethoxysilane (I-1)

In a 100 ml autoclave were charged 13.0 g (0.191 mole) of cyclopentene, 23.5 g (0.173 mole) of trichlorosilane and 25 μl of a 0.077 m mole/ml chloroplatinic acid solution in isopropyl alcohol (platinum content 1.92×10 mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged the cyclopentyl trichlorosilane prepared above and 300 ml of hexane, to which a mixture of 47.0 g (0.59 mole) of pyridine and 14.8 g (0.246 mole) of isopropyl alcohol was added dropwise over a period of 30 minutes at room temperature under stirring. After refluxing for further 2 hours, 22.9 g (0.496 mole) of ethanol were added and refluxing was continued for further 1 hour and then the reaction was ended.

Figure 1:
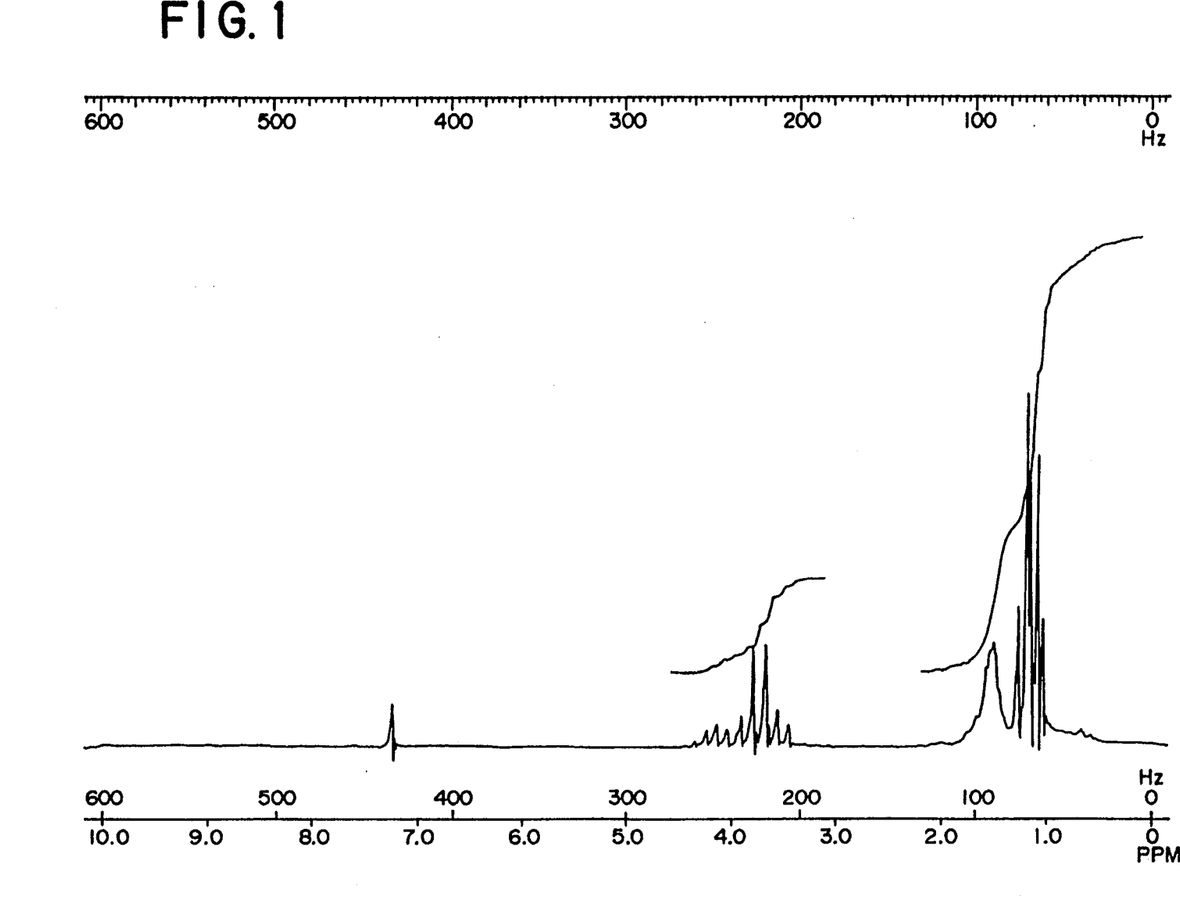
FIGS. 1 and 2 are charts of $^1$H-NMR and IR, respectively, on compound (I-1) obtained in Example 1.
Figure 2:
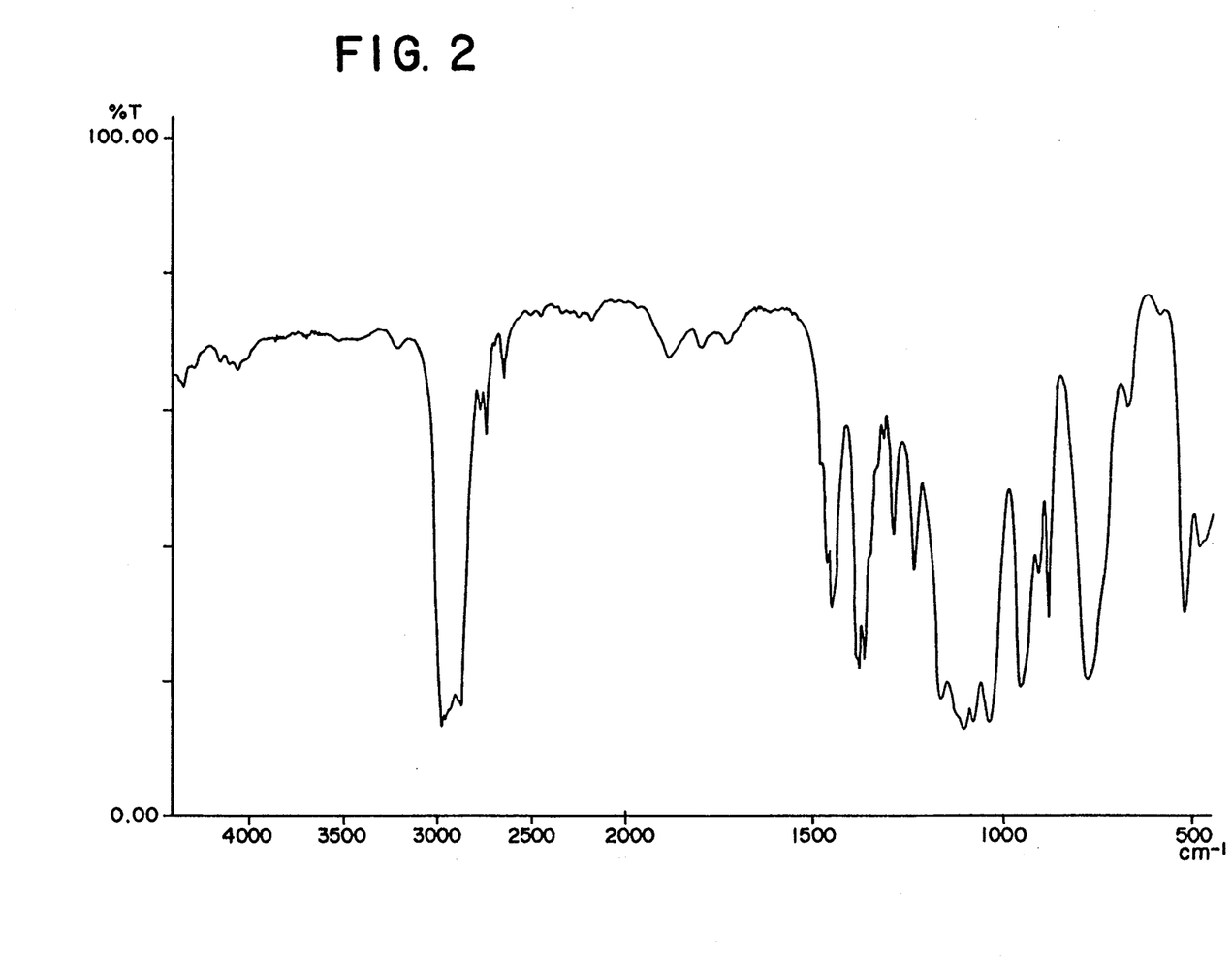

After a salt formed was filtered off and hexane was distilled off, a liquid of 27.7 g (0.112 mole) with a boiling point of 115° C./92 mmHg was obtained by vacuum distillation. This product was confirmed to be isopropoxy cyclopentyl diethoxysilane by GC-MS, $^1$H-NMR and IR. FIGS. 1 and 2 are the charts of $^1$H-NMR and IR, respectively. The yield was 65%.

The GC-MS measurement results, m/e vs. spectral intensity ratios in parentheses, are as follows: 79(19), 107(18), 135(70), 163(14), 177(100).

Example 2

Another Preparation of Isopropoxy Cyclopentyl Diethoxysilane (I-1)

In a 500 ml three-neck flask provided with a magnetic stirrer and a reflux condenser were charged 19.6 g (0.0841 mole) of cyclopentyl triethoxysilane, 98.0 g (1.63 mole) of isopropyl alcohol and 198.7 mg (2.92 m mole) of sodium ethoxide, which were then reacted with each other at room temperature for 2 hours under stirring. Then, trimethylchlorosilane was added to neutralize the alkali. Then, 9.56 g (0.0388 mole) of isopropoxy cyclopentyl diethoxysilane were obtained by vacuum distillation. Its structure was confirmed as in Example 1. Tile yield was 46%.

Example 3

Preparation of sec-Butoxy Cyclopentyl Diethoxysilane (I-2)

In a 100 ml autoclave were charged 15.0 g (0.220 mole) of cyclopentene, 26.9 g (0.198 mole) of trichlorosilane and 25 μl of a 0.077 m mole/ml chloroplatinic acid solution in isopropyl alcohol (platinum content 1.92×10$^{-6}$ mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged tile cyclopentyl trichlorosilane prepared above and 300 ml of hexane, to which a mixture or 53.1 g (0.67 mole) of pyridine and 22.6 g (0.30 mole) of sec-butyl alcohol was added dropwise over a period of 30 mixtures at room temperature under stirring.

After refluxing for further 2 hours, 26.9 g (0.584 mole) of ethanol were added and refluxing was continued for further 1 hour and then the reaction was ended.

Figure 3:
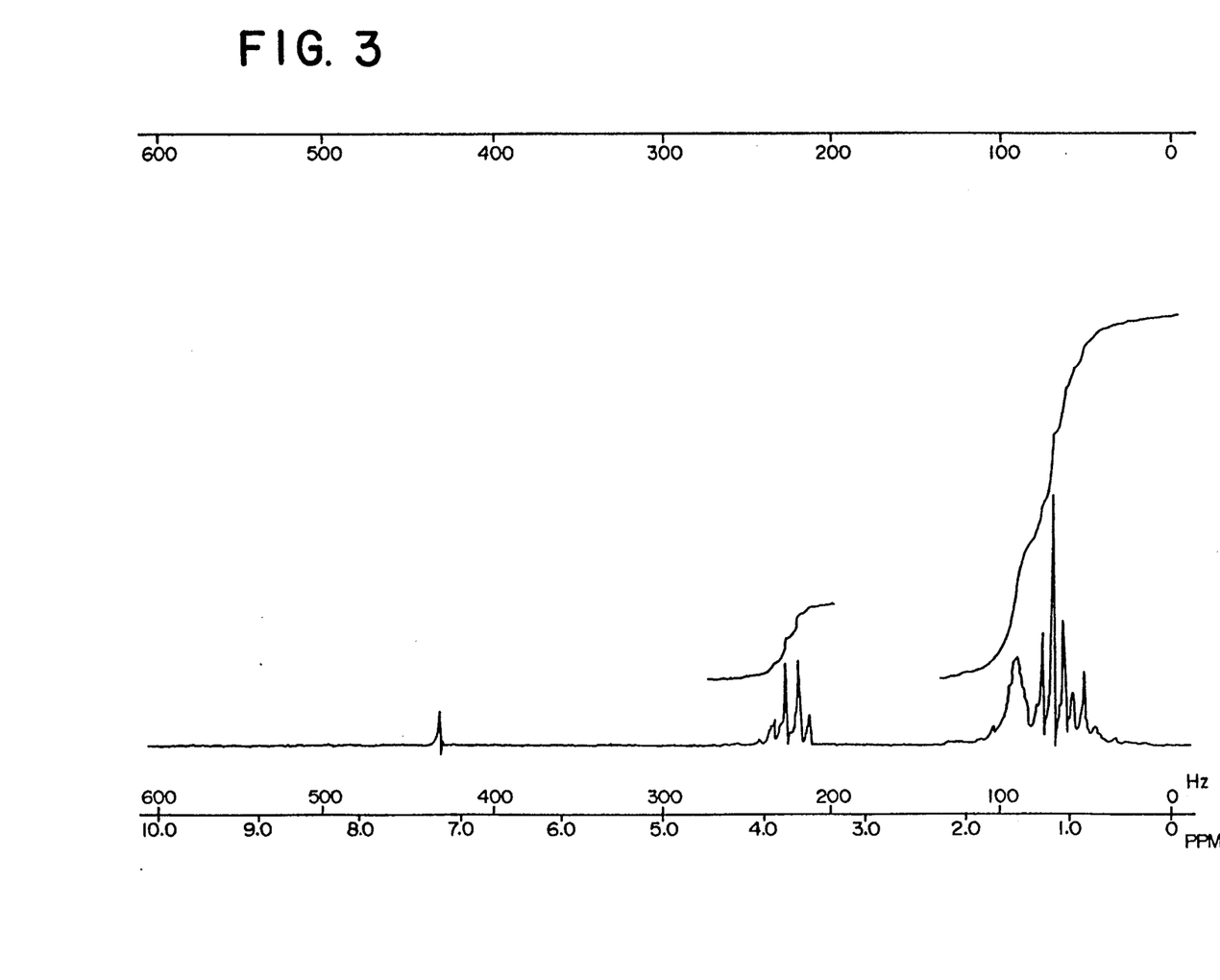
FIGS. 3 and 4 are charts of $^1$H-NMR and IR, respectively, on compound (I-2) obtained in Example 3.
Figure 4:
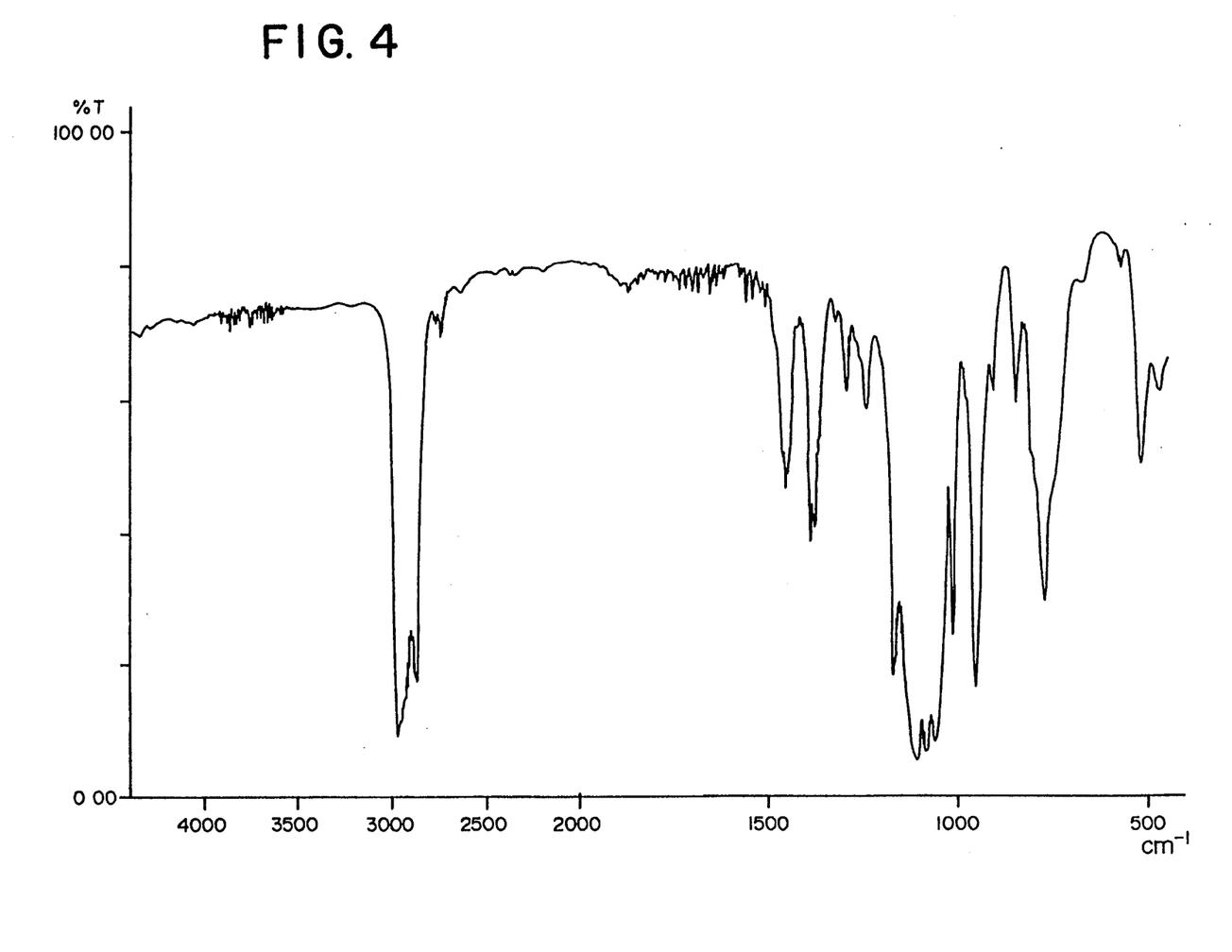

After a salt formed was filtered off and hexane was distilled off, a liquid of 37.3 g (0.143 mole) with a boiling point of 130° C./20 mmHg was obtained by vacuum distillation. This product was confirmed to be sec-butoxy cyclopentyl diethoxysilane by GC-MS, $^1$H-NMR and IR. FIGS. 3 and 4 are the charts of $^1$H-NMR and IR, respectively. The yield was 72%.

The GC-MS measurement results, m/e vs. spectral intensity ratios in parentheses, are as follows: 231(17), 191(83), 187(17), 163(38), 135(100), 119(15), 107(20), 79(30), 63(28).

Example 4

Another Preparation of sec-Butoxy Cyclopentyl Diethoxysilane (I-2)

In a 500 ml three-neck flask provided with a magnetic stirrer and a reflux condenser were charged 29.6 g (0.127 mole) of cyclopentyl triethoxysilane, 151.1 g (2.04 mole) of sec-butyl alcohol and 286.5 mg (4.21 m mole) of sodium ethoxide, which were then reacted with each other in an oil bath of 50° C. for 10 hours under stirring. Then, trimethylchlorosilane was added to neutralize the alkali. Then, 24.2 g (0.0931 mole) of sec-butoxy cyclopentyl diethoxysilane were obtained by vacuum distillation. Its structure was confirmed as in Example 1. The yield was 73%

Example 5

Preparation of tert-Butoxy Cyclopentyl Diethoxysilane (I-3)

In a 100 ml autoclave were charged 14.0 g (0.206 mole) of cyclopentene, 25.3 g (0.187 mole) of trichlorosilane and 25 μl of a 0.077 m mole/ml chloroplatinic acid solution in isopropyl alcohol (platinum content 1.92×10$^{-6}$ mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged the cyclopentyl trichlorosilane prepared above and 300 ml of hexane, to which a mixture of 50.6 g (0.64 mole) of pyridine and 19.8 g (0.267 mole) of tert-butyl alcohol was added dropwise over a period of 30 minutes at room temperature under stirring.

After 2 hours reflux, 25.6 g (0.555 mole) of ethanol were added and reflux was continued for further one hour and then the react ion was ended.

Figure 5:
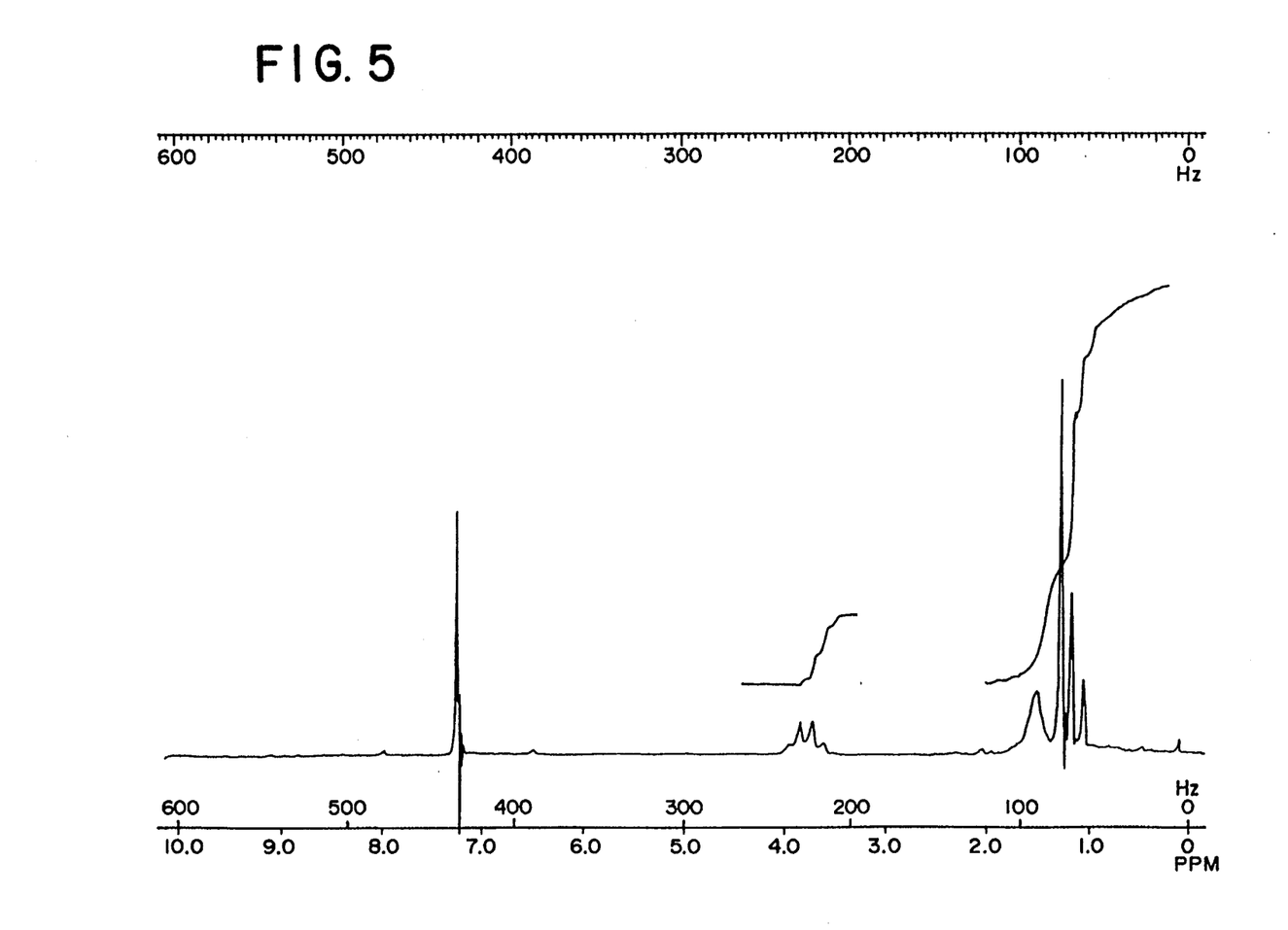
FIGS. 5 and 6 are charts of $^1$H-NMR and IR, respectively, on compound (I-3) obtained in Example 5.
Figure 6:
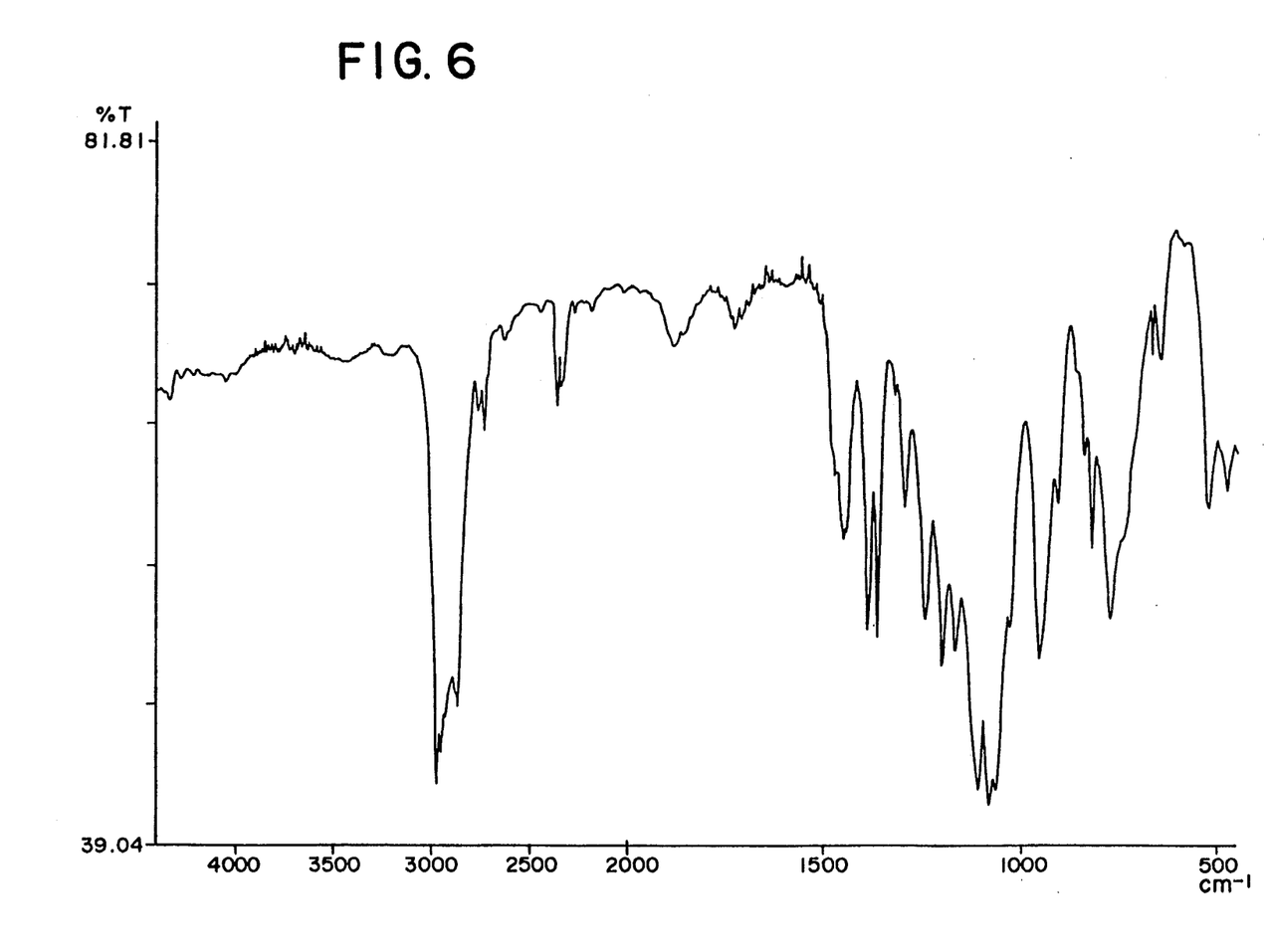

After a salt formed was filtered off and hexane was distilled off, a liquid of 25.5 g (0.0979 mole) with a boiling point of 90.1° C./8.1 mmHg was obtained by vacuum distillation. This product was confirmed to be tert-butoxy cyclopentyl diethoxysilane by GC-MS, $^1$H-NMR and IR. FIGS. 5 and 6 are the charts of $^1$H-NMR and IR, respectively. The yield was 52%.

The GC-MS measurement results, m/e vs. spectral intensity ratios in parentheses, are as follows: 79(17), 107(13), 135(100), 187(16), 191(32), 245(17).

Example 6

Another Preparation of tert-Butoxy Cyclopentyl Diethoxysilane (I-3)

In a 500 ml three-neck flask provided with a magnetic stirrer and a reflux condenser were charged 29.3 g (0.129 mole) of cyclopentyl triethoxysilane, 165.9 g (2.24 mole) of tert-butyl alcohol and 2.06 g (30.3 m mole) of sodium ethoxide, which were then reacted with each other in an oil bath of 85° C. for 24 hours under stirring. Then, trimethylchlorosilane was added to neutralize the alkali. Then, 21.6 g (0.0828 mole) of tert-butoxy cyclopentyl diethoxysilane were obtained by vacuum distillation. Its structure was confirmed as in Example 1. The yield was 64%.

Example 7

Preparation of tert-Amyloxy Cyclopentyl Diethoxysilane (I-4)

In a 100 ml autoclave were charged 15.2 g (0.223 mole) of cyclopentene, 27.2 g (0.201 mole) of trichlorosilane and 25 μl of a 0.077 m mole/ml chloroplatinic acid solution in isopropyl alcohol (platinum content $1.92 \times 10^{-6}$ mole), which were then stirred at 150° C.; for 30 minutes. Cyclopentyl trichlorosilane was obtained quantitatively.

In a 500 ml three-neck flask provided with a magnetic stirrer, a reflux condenser and a dropping funnel were charged the cyclopentyl trichlorosilane prepared above and 300 ml of hexane, to which a mixture of 54.2 g (0.69 mole) of pyridine and 25.2 g (0.29 mole) of tert-amyl alcohol was added dropwise over a period of 30 minutes at room temperature under stirring.

After 2 hours reflux, 27.7 g (0.602 mole) of ethanol were added and reflux was continued for further one hour and then the react ion was ended.

Figure 7:
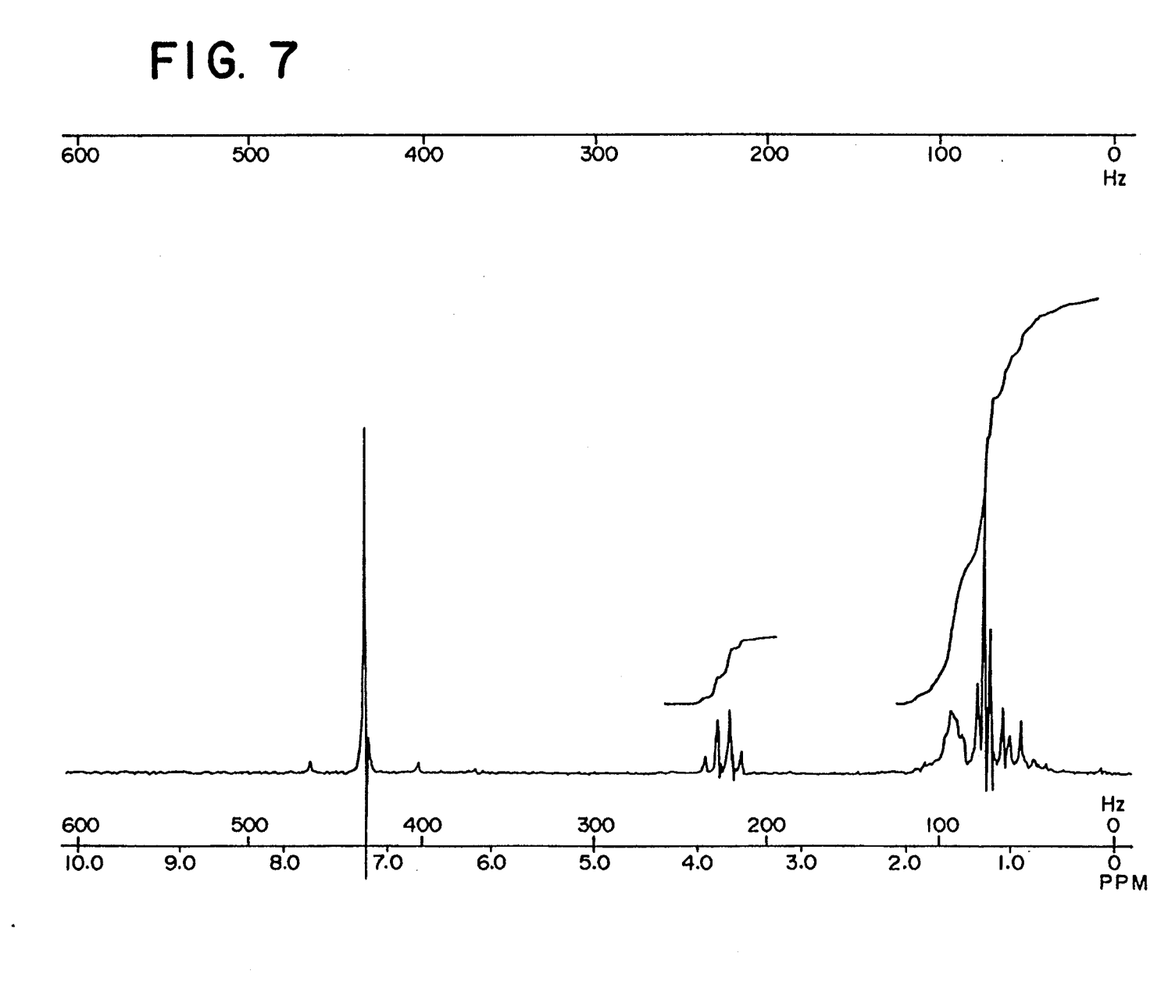
FIGS. 7 and 8 are charts of $^1$H-NMR and IR, respectively, on compound (I-4) obtained in example 7.
Figure 8:
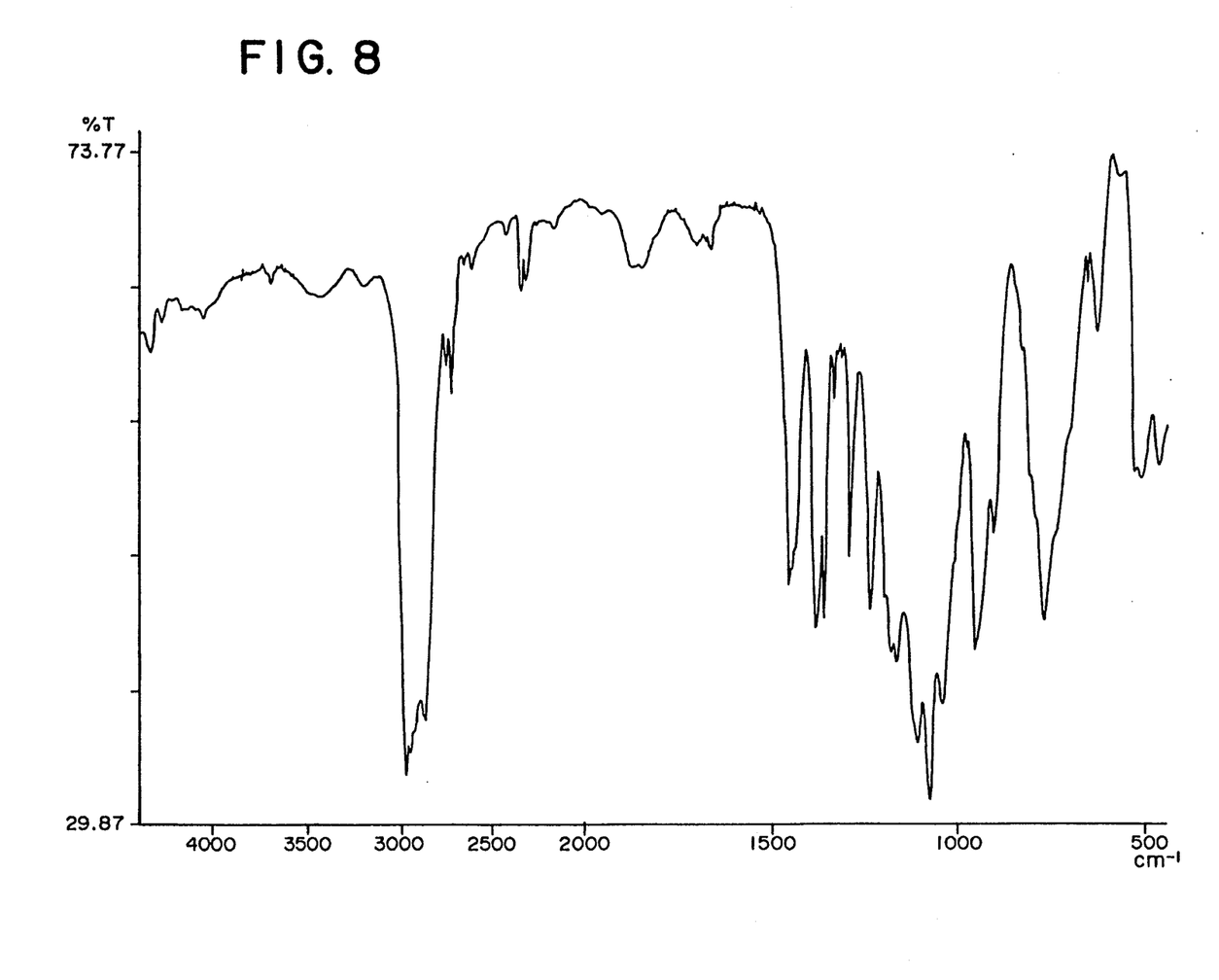

After a salt formed was filtered off and hexane was distilled off, a liquid of 38.7 g (0.141 mole) with a boiling point of 132° C./24 mmHg was obtained by vacuum distillation. This product was confirmed to be tert-amyloxy cyclopentyl diethoxysilane by GC-MS, $^1$H-NMR and IR. FIGS. 7 and 8 are the charts of $^1$H-NMR and IR, respectively. The yield was 70%.

The GC-MS measurement results, m/e vs. spectral intensity ratios in parentheses, are as follows: 63(28), 79(30), 119(15), 135(100), 159(12), 177(10), 187(28), 205(15), 245(24).

Example 8

Another Preparation of tert-Amyloxy Cyclopentyl Diethoxysilane (I-4)

In a 100 ml three-neck flask provided with a magnetic stirrer and a reflux condenser were charged 20.5 g (0.0882 mole) of cyclopentyl triethoxysilane, 128 g (1.46 mole) of tert-amyl alcohol and 0.953 g (14.0 m mole) of sodium ethoxide, which were then reacted with each other in an oil bath of 105° C. for 24 hours under stirring. Subsequently, trimethylchlorosilane was added to neutralize the alkali. Then, 19.0 g (0.0693 mole) of tert-amyloxy cyclopentyl diethoxysilane were obtained by vacuum distillation. Its structure was confirmed as in Example 1. The yield was 79%.

What we claim is:

1. A silane compound represented by the following formula (I):

wherein R represents an organic group selected from the group consisting of isopropyl, sec-butyl, tert-butyl and tert-amyl groups.

2. A process for tile preparation of the silane compound represented by the following formula (I):

wherein R represents an organic group selected from the group consisting of isopropyl, sec-butyl, tert-butyl and tert-amyl groups, characterized in that cyclopentyl trihalosilane is reacted with ROH, wherein R has the same meaning as above, and then a resultant reaction product is reacted with ethanol.

3. The process as claimed in claim 2, wherein the reactions are conducted in the presence of a hydrogen halide acceptor.

4. The process as claimed in claim 3, wherein the hydrogen halide acceptor is a tertiary amine or a nitrogen-containing heterocyclic compound.

5. The process as claimed in claim 2, wherein cyclopentyl trihalosilane is reacted with ROH at a temperature of 20° to 100° C. for 10 minutes to 5 hours and then the resultant reaction product is reacted with ethanol at a temperature of 0° to 100° C. for 10 minutes to 5 hours.

6. The process as claimed in claim 5, wherein the first reaction is conducted at a temperature of 40° to 70° C. for 0.5 to 2 hours, and the second reaction at a temperature of 10° to 60° C. for 0.5 to 2 hours.

7. A process for the preparation of the silane compound represented by the following formula (I):

wherein R represents an organic group selected from the group consisting of isopropyl, sec-butyl, tert-butyl and tert-amyl groups, characterized in that cyclopentyl triethoxysilane is reacted with ROH via exchange of alkoxy groups to introduce an OR group into said silane compound, wherein R has the same meaning as above.

8. The process as claimed in claim 7, wherein the reaction is conducted at a temperature of 0° to 100° C. in the case of R being an isopropyl or tert-butyl group, or 0° to 150° C. in the case of R being a sec-butyl or tert-amyl group, for 10 minutes to 20 hours in the case of R being all isopropyl or sec-butyl group, 10 minutes to 50 hours in the case of R being a tert-butyl group, or 10 minutes to 30 hours in the case of R being a tert-amyl group.

* * * * *